United States Patent
Schöttli

(10) Patent No.: US 6,562,009 B1
(45) Date of Patent: May 13, 2003

(54) PUMP PISTON FOR A DISPOSABLE SYRINGE

(75) Inventor: Martin Schöttli, Basadingen (CH)

(73) Assignee: Schöttli AG, Diessenhofen (CH)

( * ) Notice: Subject to any disclaimer, the term of this patent is extended or adjusted under 35 U.S.C. 154(b) by 129 days.

(21) Appl. No.: 09/709,906

(22) Filed: Nov. 9, 2000

(30) Foreign Application Priority Data

Nov. 12, 1999 (CH) .............................................. 2068/99

(51) Int. Cl.⁷ .............................................. A61M 5/315
(52) U.S. Cl. ...................................... 604/218; 604/152
(58) Field of Search ................................ 604/110, 152, 604/218, 82, 187, 221, 222

(56) References Cited

U.S. PATENT DOCUMENTS

| | | | | |
|---|---|---|---|---|
| 3,993,061 A | * | 11/1976 | O'Leary ..................... | 604/152 |
| 4,201,209 A | | 5/1980 | LeVeen et al. | |
| 4,469,482 A | * | 9/1984 | Lissenburg et al. ......... | 604/187 |
| 4,932,941 A | * | 6/1990 | Min et al. .................. | 604/110 |
| 5,147,328 A | * | 9/1992 | Dragosits et al. ........... | 604/218 |
| 5,257,976 A | * | 11/1993 | Fenet et al. ................. | 604/110 |
| 5,496,285 A | * | 3/1996 | Schumacher et al. ....... | 604/218 |
| 5,527,285 A | * | 6/1996 | Lenz ......................... | 604/110 |
| 5,540,660 A | * | 7/1996 | Jenson ....................... | 604/110 |
| 5,695,465 A | * | 12/1997 | Zhu ........................... | 604/82 |
| 5,902,276 A | | 5/1999 | Namey, Jr. | |
| 6,196,997 B1 | * | 3/2001 | Saito ......................... | 604/110 |
| 2001/0041867 A1 | * | 11/2001 | Schottli ...................... | 604/110 |

FOREIGN PATENT DOCUMENTS

| | | | | |
|---|---|---|---|---|
| DE | 3901484 | * | 12/1989 | ............ A61M/5/31 |
| FR | 2 618 683 A1 | | 2/1989 | |

* cited by examiner

Primary Examiner—Teresa Walberg
Assistant Examiner—Leonid Fastovsky
(74) Attorney, Agent, or Firm—Akin Gump Strauss Hauer & Feld, L.L.P.

(57) ABSTRACT

A plastic pump piston is provided for a disposable syringe, wherein the disposable syringe has a syringe cylinder which is constructed with a needle cone on one end thereof and at least one gripping plate on the other end thereof, and having a sealing element on the front end of a shaft of the pump piston. The sealing element is made of a material having a higher elasticity than the pump piston material and is molded onto the pump piston in the same mold after the pump piston is injection molded.

7 Claims, 3 Drawing Sheets

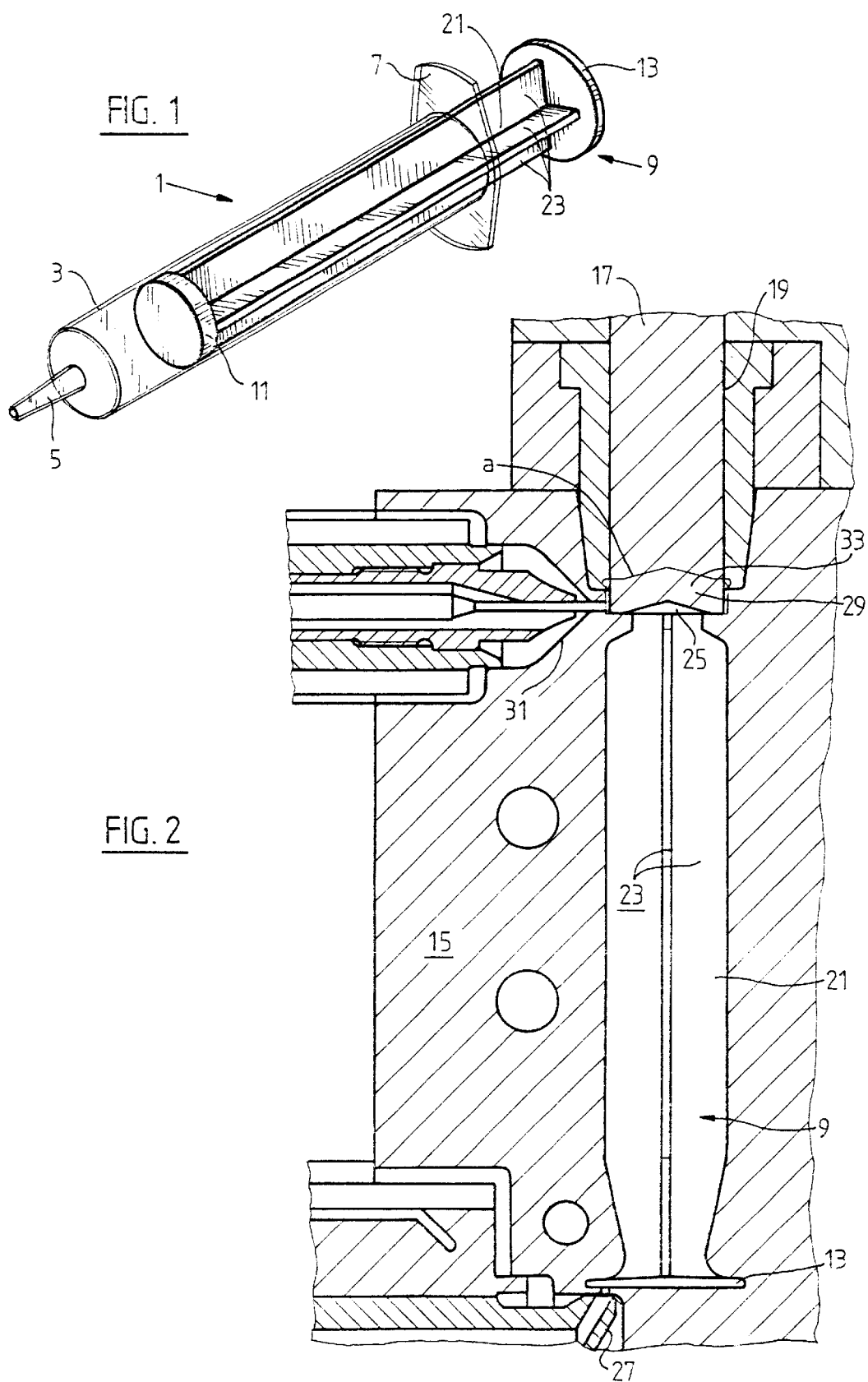

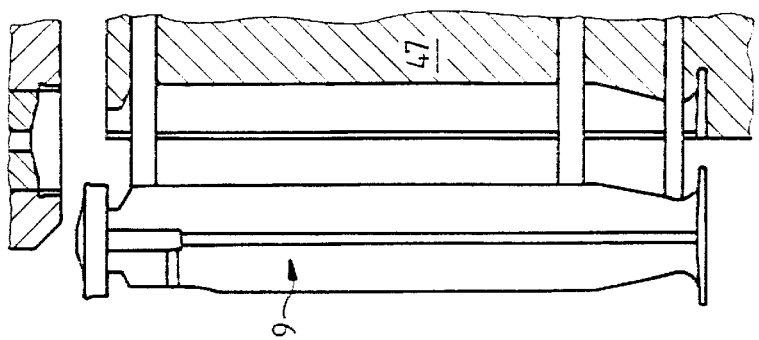
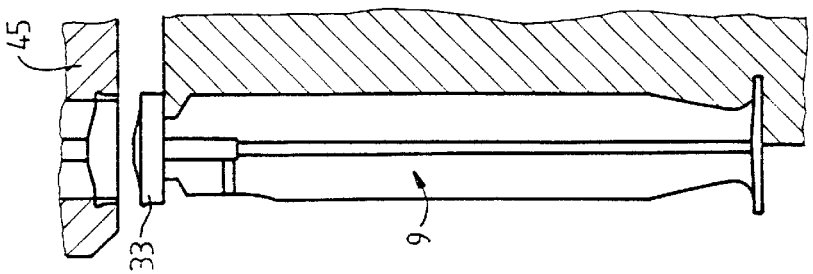
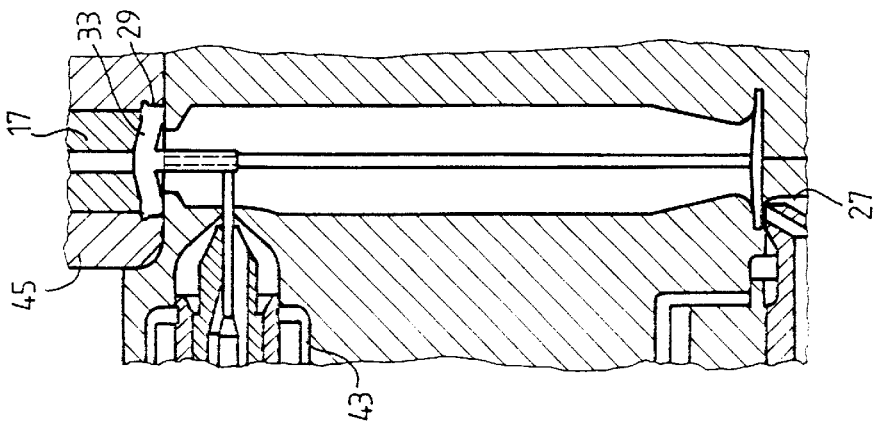
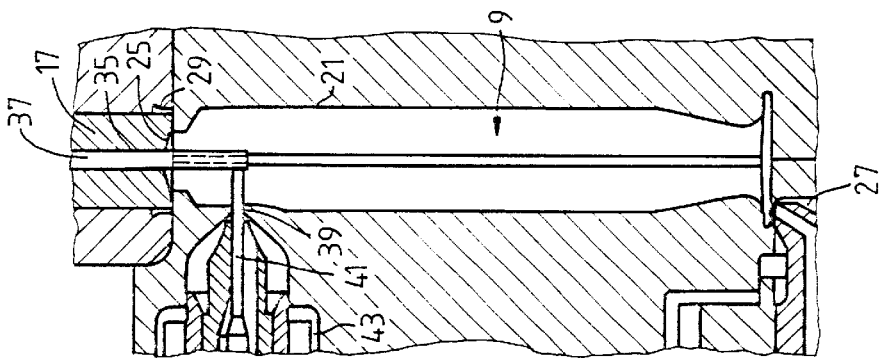

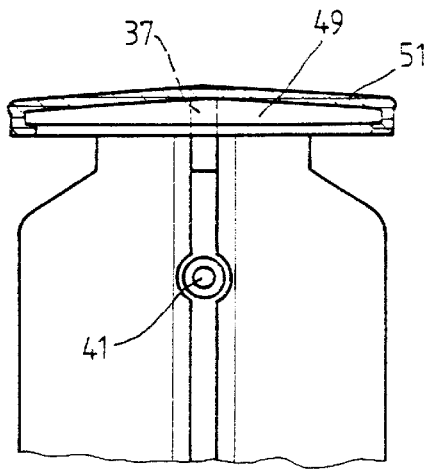
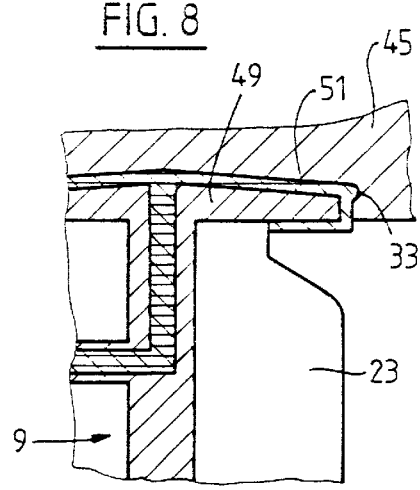
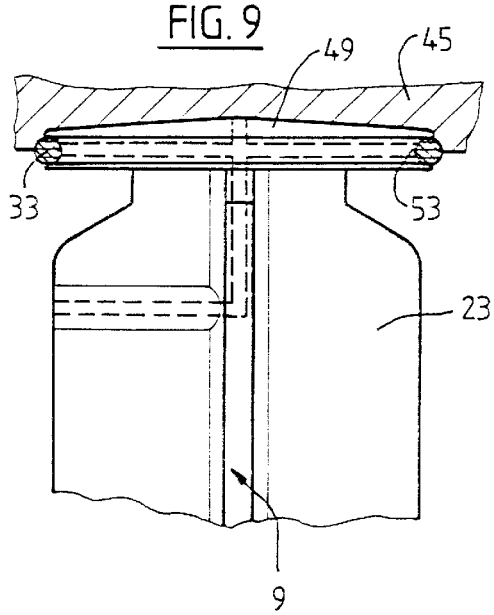
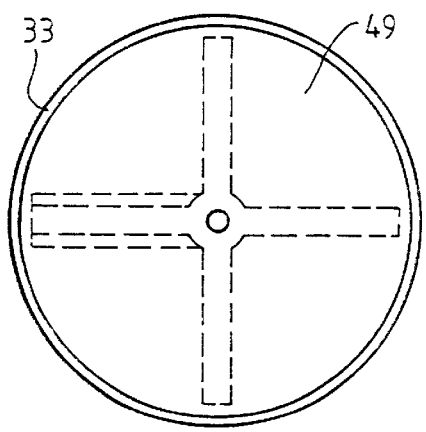

PUMP PISTON FOR A DISPOSABLE SYRINGE

BACKGROUND OF THE INVENTION

The invention relates to a process for manufacturing a pump piston for a disposable syringe made of plastic by injection molding. The invention further relates to a pump piston for a disposable syringe, made of plastic according to the process. The disposable syringe comprises a syringe cylinder having a needle cone on one end thereof and at least one gripping plate on the other end thereof, and a sealing element on the front end of the shaft of the pump piston.

Disposable syringes are needed in large quantities in hospitals and doctor's practices. They are known from the prior art in countless embodiments as two-part and three-part plastic syringes. The two-part syringes include a pump piston with a piston rod and a press plate. The syringe cylinder has a needle cone on its one end and gripping plates on its other end. The seal between the piston and the cylinder results from a somewhat larger diameter of the piston relative to the inner diameter of the cylinder.

Pump pistons having elastic lips constructed on their peripheries are also known from the prior art.

In the three-part syringes an additional sealing ring made of an elastomer sits on the piston, which must be set on later, i.e., after the manufacture of the pump piston and before its insertion into the cylinder. Three-part disposable syringes have the advantage that the friction between the piston and the cylinder is smaller, so that a uniform advance of the piston can be ensured during injection.

It is also known to silicone-treat the inner surface of the cylinder, i.e., the running surface for the piston, in order to ensure a smooth, uniform sliding of the piston. In this manner, however, small quantities of the silicone sliding agent employed get into the body of the human or the animal. This is not desirable in any case.

BRIEF SUMMARY OF THE INVENTION

An object of the present invention is to create a pump piston for a disposable syringe, which can be manufactured in a cost-effective way, as well as a process for manufacturing a pump piston for a syringe.

This object is achieved by a process for manufacturing a pump piston for a disposable syringe made of plastic, in which the shaft and the press plate on one end thereof are injection molded and a sealing ring receptacle is injection molded on the other end of the shaft from a first plastic component using a first injection molding nozzle, and within the same mold after enlarging the cavity an elastic sealing element made of a second plastic component is subsequently injection molded on the front end of the shaft.

This object is further achieved by a pump piston for a disposable syringe, made of plastic according to the above process, wherein the disposable syringe has a syringe cylinder which is constructed with a needle cone on one end thereof and at least one gripping plate on the other end thereof, and a sealing element on the front end of the shaft of the pump piston. The sealing element is made of a material having a higher elasticity than the pump piston material and is molded onto the pump piston in the same mold after the piston is injection molded, so that the sealing element cannot be detached.

The pump piston can be injected molded in two steps, but within the same injection mold, from two different, functionally-suitable materials. The manufacture of such a pump piston is very cost-effective, and no manual assembly activities, namely the setting down of a sealing ring, must be performed. The soft plastic material that forms the seal can not jump off of the piston, so that its assembly into the cylinder is possible without later verification/checking. The seal is ensured in any case.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 1 is a perspective representation of a disposable syringe with partially inserted pump piston;

FIG. 2 is a cross-section through a mold for injection molding of the pump piston for disposable syringes (direct injection molding of the second component);

FIGS. 3–6 each show one manufacturing stage during injection molding of the second component through the first component;

FIG. 7 is a section through the pump piston in another embodiment of a pump piston;

FIG. 8 is a cross-section through the front part of a pump piston, made in a mold according to FIG. 7;

FIG. 9 is a section through the front part of a pump piston in another embodiment of the invention; and FIG. 10 is a plan of the pump piston in FIG. 9.

DETAILED DESCRIPTION OF THE INVENTION

The disposable syringe 1 in FIG. 1 includes a pump cylinder 3 on whose lower (front) end a needle cone 5 is constructed and on whose upper (rear) end radially projecting gripping plates 7 are molded on. Into the cylinder 3 a pump piston 9 is inserted, on whose front end a seal 11 is mounted and its rear end has a press plate 13.

The invention described in the following involves only the pump piston 9; the cylinder 3 and its construction are taken from the prior art and not explained further.

The pump piston 9 according to the invention includes a shaft 21, which can comprise four ribs 23 arranged in a star shape, a cone or taper 25 on the front end, and the gripping or press plate 13 on the rear end. A seal is non-releasably connected with the cone 25. The seal can completely or partially (FIGS. 7 and 8) surround the cone 25 or have the shape of an O-ring (FIG. 9).

In the following, the manufacture of the pump piston 9 is explained using FIGS. 2 to 10. In FIGS. 2 to 5 different areas of the hollow spaces in the mold are designated with the same reference numerals as the parts of the pump piston.

In an injection molding mold 15, in which the pump piston 9 is manufactured, a slide 17 in the shape of a cylinder is installed and is axially slidable along the longitudinal axis of the pump piston 9 in a bore 19 in the injection mold 15. The drive instruments for the slide 17 are not shown. When the slide 17 has been moved forward, downward as shown in FIG. 2 and as presented at the beginning of the injection molding operation, the cavity 21 in the mold 15 is designed in such a way that the pump piston 9 results, on whose upper (front) end the four ribs 23 of the shaft 21 carry the flat cone 25 as a sealing element receptacle. The injection molding of the liquid plastic is performed in the cavity for the pump piston 9 with a nozzle 27, which injects plastic into the area of the press plate 13, which forms the lower (rear) end of the shaft 21.

After the injection molding of the plastic for the shaft 21, the press plate 13 and the cone 25 with the first nozzle 27, and after a short pause for solidification, the slide 17 is pulled back (upward in FIG. 2) axially and thereby creates a new cavity 29 (outline in fine lines in FIG. 2), which closes off the shaft 21 above the cone 25. In this additional cavity 29 a second plastic component with preferably high elasticity and good slide properties is injected through a second nozzle 31. In this additional cavity 29 a sealing element 33 then results, for example a sealing plate or a sealing ring, which is permanently connected with the cone 25 of the pump piston 9. After the solidification of the plastic forming the sealing element 33, the pump piston 9 can be taken out of the mold. The pump piston 9 generated in this manner can be inserted into the cylinder 3 of the disposable syringe 1 without further processing. The sealing element 33 having a cylinder sheath-shaped periphery in FIGS. 4 to 6 can, of course, also be provided with surrounding grooves (labyrinths).

In the second embodiment of the invention for the generation of sealing element 33, for example the sealing plate or the sealing ring on the front end of the pump piston 9, an axial needle bore 35 is constructed in the slide 17, through which a needle 37 can be inserted axially into the cavity 21 for the pump piston 9. At a right angle to the first needle bore 35, a second needle bore 39 is constructed, spaced from the end of the cavity 21, in which a second needle 41, which is part of an injection molding nozzle 43, is guided and can be inserted into the cavity 21.

During the injection molding of the shaft 21 of the pump piston 9, both needles 37 and 41 are shoved forward and contact each other. In this manner, a recess running at a right angle appears in the shaft 21 of the pump piston 9. This functions in the second process step, for the manufacturing according to FIG. 4, so that in the additional cavity 29, after the slide 17 is pulled back, the second plastic component for the generation of the sealing element can be injection molded with the nozzle 43. After the completion of the pump piston 9, the channels, constructed at the beginning by the needles 37 and 41 being moved forward in the shaft 21, are filled with the material that makes the sealing element 31, 51.

To take the pump piston 9 made from two components out of the mold, the mold part 45 containing the slide 17 is first guided away toward the top, and thereafter the mold part 47, lying to the right of the cavity 21 in FIGS. 3 to 6, is moved to the side.

Also, after it is taken out of the mold, this pump piston 9 can be inserted without additional processing into the cylinder 3 of the disposable syringe 1.

The sealing plates or sealing rings 33 in the first two embodiments according to FIGS. 2 to 6 are made completely of the second elastic component, which is injection molded onto the cone 25 at the end of the shaft.

In FIGS. 7 to 10 a pump piston 9 is shown, in which the elastic component for the sealing element is constructed as a covering (FIGS. 7 and 8) or as a surrounding ring (FIGS. 9 and 10).

In both embodiments, first of all, on the front end of the ribs 23 a discshaped plate 49 is constructed in the first operation. Then, the slide 17 is pulled back a few hundredths of a millimeter, and the second plastic component is supplied through the bores generated by the two needles 37 and 41 (as shown in FIGS. 3 and 4). In this manner, a thin sealing element, i.e., a very elastic sealing skin 51, is generated, which completely covers the plate 49. By suitable shaping of the upper mold part 45, a torusshaped sealing ring 33 is formed on the periphery of the plate 49.

In the embodiment of the invention according to FIGS. 9 and 10, in the periphery of the plate 49, a surrounding groove 53 was generated in the first process step, which in the second process step is filled by the second soft plastic component and a sealing ring 33 is formed, as is known as an O-ring. The sealing ring 33 is, however, non-releasably connected with the pump piston, and need not be mounted afterwards.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:
1. A plastic pump piston for a disposable syringe, comprising:
   a syringe cylinder having a needle cone on a front end of the cylinder and at least one gripping plate on a rear end of the cylinder;
   a shaft having a seal receptacle on a front end of the shaft and a press plate on a rear end of the shaft, wherein the shaft, press plate and seal receptacle are injection molded from a first plastic material as one piece; and
   an elastic sealing element comprising a second plastic material having a higher elasticity than the first plastic material, wherein the sealing element is non-releasably injection molded onto the sealing receptacle as a second piece.

2. The pump piston according to claim 1, wherein the seal receptacle comprises a cone or a disc-shaped plate, which carries the sealing element.

3. The pump piston according to claim 2, wherein the sealing element completely surrounds or covers the disc-shaped plate.

4. The pump piston according to claim 2, wherein the sealing element is connected to a periphery of the plate.

5. The pump piston according to claim 4, wherein the sealing element is formed in a surrounding groove in the periphery of the plate and has a round cross-section.

6. The pump piston according to claim 1, wherein the shaft has at least one first injection molding channel running radially through a rib of the pump piston, and the channel is filled with the second plastic material for the sealing element.

7. The pump piston according to claim 1, wherein the shaft has a second injection molding channel running axially of the pump piston, and the channel is filled with the second plastic material for the sealing element.

* * * * *